United States Patent [19]
Weng

[11] Patent Number: 5,804,653
[45] Date of Patent: Sep. 8, 1998

[54] POLYVINYL ALCOHOL COMPOUND

[75] Inventor: Dexi Weng, Brooklyn, N.Y.

[73] Assignee: Playtex Products, Inc., Westport, Conn.

[21] Appl. No.: 812,629

[22] Filed: Mar. 7, 1997

[51] Int. Cl.$^6$ .......................... C08F 16/06; C08F 116/06; C08G 63/48; C08G 63/91
[52] U.S. Cl. ................................ 525/56; 525/57; 525/58; 524/47; 604/372; 264/239
[58] Field of Search .................................. 525/56, 57, 58, 525/60; 524/47; 604/372, 367; 264/239

[56] References Cited

U.S. PATENT DOCUMENTS

| | | |
|---|---|---|
| 3,717,149 | 2/1973 | Morane . |
| 3,724,462 | 4/1973 | Hanke . |
| 3,796,219 | 3/1974 | Hanke . |
| 3,882,196 | 5/1975 | Hanke . |
| 3,882,869 | 5/1975 | Hanke . |
| 3,911,917 | 10/1975 | Hanke . |
| 3,954,104 | 5/1976 | Kraskin et al. . |
| 4,099,976 | 7/1978 | Kraskin et al. . |
| 4,140,668 | 2/1979 | Sumi et al. . |
| 4,309,510 | 1/1982 | Kleber . |
| 4,323,492 | 4/1982 | Zimmermann et al. . |
| 4,372,311 | 2/1983 | Potts . |
| 4,389,506 | 6/1983 | Hassall, Jr. . |
| 4,452,178 | 6/1984 | Zimmermann et al. . |
| 4,454,194 | 6/1984 | Luebbe, Jr. . |
| 4,469,867 | 9/1984 | Cattaneo . |
| 4,478,971 | 10/1984 | Billard . |
| 4,479,997 | 10/1984 | Masterson et al. . |
| 4,482,599 | 11/1984 | Luebbe, Jr. . |
| 4,488,158 | 12/1984 | Wirnowski . |
| 4,536,532 | 8/1985 | Miller et al. . |
| 4,547,329 | 10/1985 | Dombroski et al. . |
| 4,611,019 | 9/1986 | Lutzmann et al. . |
| 4,618,648 | 10/1986 | Marten . |
| 4,656,216 | 4/1987 | Muller et al. . |
| 4,675,360 | 6/1987 | Marten . |
| 4,692,494 | 9/1987 | Sonenstein . |
| 4,708,999 | 11/1987 | Marten . |
| 4,849,256 | 7/1989 | Newman et al. . |
| 4,900,299 | 2/1990 | Webb . |
| 4,950,513 | 8/1990 | Mehra . |
| 5,002,526 | 3/1991 | Herring . |
| 5,028,648 | 7/1991 | Fmili et al. . |
| 5,051,222 | 9/1991 | Marten et al. . |
| 5,070,126 | 12/1991 | Toyonishi et al. . |
| 5,093,401 | 3/1992 | Claussen . |
| 5,135,475 | 8/1992 | Nakanishi et al. . |
| 5,137,969 | 8/1992 | Marten et al. . |
| 5,187,226 | 2/1993 | Kamachi et al. . |
| 5,190,712 | 3/1993 | Oishi et al. . |
| 5,206,278 | 4/1993 | Famili et al. . |
| 5,258,430 | 11/1993 | Bastioli et al. . |
| 5,262,458 | 11/1993 | Bastioli et al. . |
| 5,349,000 | 9/1994 | Robeson et al. . |
| 5,350,354 | 9/1994 | Billmers . |
| 5,360,830 | 11/1994 | Bastioli et al. . |
| 5,380,529 | 1/1995 | Heusser et al. . |
| 5,389,068 | 2/1995 | Keck . |
| 5,395,308 | 3/1995 | Fox et al. . |

FOREIGN PATENT DOCUMENTS

| | | |
|---|---|---|
| 260512 | 5/1993 | Australia . |
| 2053219 | 4/1993 | Canada . |
| 0 291 024 A2 | 11/1988 | European Pat. Off. . |
| 0 585 906 A2 | 3/1994 | European Pat. Off. . |

*Primary Examiner*—Nathan M. Nutter
*Attorney, Agent, or Firm*—Ohlandt, Greeley, Ruggiero & Perle

[57] ABSTRACT

A moldable polymeric compound containing about 50 to 99 weight percent of a polyvinyl alcohol and about 1 to 50 weight percent of an oxa acid plasticizer, suitable for molding biodegradable and water dispersible objects such as tampon applicators.

31 Claims, No Drawings

POLYVINYL ALCOHOL COMPOUND

The present invention is directed to an improved polyvinyl alcohol molding compound having excellent performance and stability. More particularly, the present invention is directed to a composition of polyvinyl alcohol and an oxa acid plasticizer that is useful in molding applications, and especially, in molding biodegradable and water dispersible tampon applicators.

BACKGROUND OF THE INVENTION

Applicators, such as tampon applicators, made of polyvinyl alcohol ("PVOH") are used in the health care and personal care industries. PVOH has frequently been used in products that require molded polymeric components to be formed via extrusion, injection or blow molding, and which products need to be biodegradable or water dispersible.

In such applications, the basic PVOH must be plasticized to be moldable. Typically a plasticizer, such as glycerol, is used. Polyethylene glycol, sorbitol, and other compounds have also been used as plasticizers. In addition, U.S. Pat. No. 5,002,526 to Herring discloses a substantially self-plasticizing modified PVOH. Of these agents, glycerol is the most common plasticizer added to PVOH.

The use of a glycerol plasticizer creates a number of drawbacks. Over time, glycerol tends to migrate out of the finished molded product, and can be found on the product surface so that the product surface is undesirably sticky. The migrated glycerol can be aesthetically unpleasant, and can interfere with the operation of the product. In addition, products formed of glycerol-plasticized PVOH tend to harden during storage due to the crystallization of the PVOH, and concomitant phase separation within the formed product. This crystallization forces additional glycerol out of the PVOH matrix. This can cause the molded product to deform, and is a direct result of the relatively high mobility of glycerol in the PVOH matrix. Furthermore, the glycerol content of the compound is difficult to maintain during molding because the glycerol tends to vaporize. It is difficult, therefore, to produce consistent output and consistent molded product quality using a glycerol-containing PVOH compound.

The present invention discloses a novel group of plasticizers suitable for use with PVOH that produce a molded product having improved stability, ease of molding, and consumer appeal. The present invention provides a PVOH compound suited to a variety of molding methods that is acceptable for commercial use.

SUMMARY OF THE INVENTION

Accordingly, it is an object of the present invention to provide a unique PVOH and plasticizer combination that avoids the problems inherent in PVOH/glycerol compositions.

It is another object of the present invention to provide a PVOH/oxa acid composition for use in molding applications.

It is a further object of the present invention to provide a tampon applicator or similar article having superior stability, strength, flexibility and quality, while remaining biodegradable and water dispersible.

It is a still further object of the present invention to provide a PVOH compound including a small amount of high molecular weight PVOHs such as those disclosed in U.S. Pat. No. 5,137,969 to Marten et al. A high molecular weight PVOH has a degree of polymerization (DP) of at least about 1200, and preferably has a DP from about 1200 to about 2400. The addition of this high molecular weight PVOH component provides greater tensile strength, flexibility and resistance to ambient humidity to the molded product. Tampon applicators made of PVOH are often subject to creep deformation on the petals, which is exacerbated by ambient moisture. The addition of the high molecular weight PVOH effectively combats this problem. Other high molecular weight polymers such as starch, polyacrylic acids, polyvinylpyrrolidone or polyethylenimine can also be used to provide resistance to petal deformation. For clarity, PVOHs having molecular weights of less than about 1200 DP are referred to herein as standard PVOHs.

Accordingly, the present invention discloses a unique moldable polymeric compound containing about 50 to 99 weight percent of a polyvinyl alcohol and about 1 to 50 weight percent of an oxa acid plasticizer such as oxa diacid, polyoxa diacid, or oxa monoacid. This mixture can be modified by the addition of a high molecular weight polyvinyl alcohol component or other similar compound.

DESCRIPTION OF THE PREFERRED EMBODIMENTS

The present invention discloses a water dispersible, biodegradable polymeric formulation with excellent aging and dimensional stability performance. The formulation can be used in injection molding of tampon applicators or other products that require dimensional stability upon aging. The formulation can also be used in extrusion and blow molding applications where superior dimensional stability is desired. The basic formulation consists of a combination of PVOH and oxa acids. The preferred polyvinyl alcohol of the present invention has the general formula:

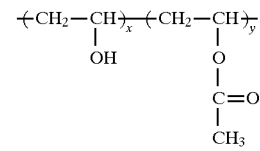

where x=about 40 to about 100 mole percent, and y=up to about 60 mole percent.

Preferred plasticizers of the present invention include oxa monoacids, oxa diacids, diglycolic acids, other linear carboxylic acids with at least one ether group distributed along a linear chain thereof, and a combination thereof. These plasticizers have higher boiling and flashing points and stronger hydrogen bonding properties than does glycerol, yet they meet the other requirements for successful PVOH plasticizers, such as compatibility with PVOH, permanence and flexibility in the finished product. For example, the boiling points (where available) and flash points of certain plasticizers are as follows:

| Plasticizer | Boiling Point (°C.) | Flash Point (°C.) |
|---|---|---|
| 3,6-dioxaheptanoic acid | 107 | >180 |
| 3,6,9-trioxadecanoic acid | 140 | >165 |
| 3,6,9-trioxaundecanedioic acid | N/A | >200 |
| polyglycolic acids | N/A | >200 |

Most preferred plasticizers of the present invention include oxa diacids of the following formula:

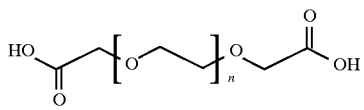

where n=0 to 1000. If n>3, this diacid is also called polyoxa diacid.

A preferred composition according to the present invention comprises about 50 to about 99% of polyvinyl alcohol, about 1 to about 50% of oxa diacid or diglycolic acid or oxa monoacid, or a combination thereof. Too little plasticizer would not flexibilize the PVOH sufficiently for use in tampon applicators.

The preferred diglycolic acid is of the following formula:

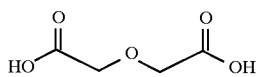

A further preferred composition according to the present invention includes a small amount of high molecular weight PVOHs, such as those disclosed in U.S. Pat. No. 5,137,969 to Marten et al. The addition of this component provides greater tensile strength, flexibility and resistance to ambient humidity to the molded product. The high molecular weight PVOH is preferably added to the composition at about 1 to about 40% by weight of the composition. Other high molecular weight polymers such as starch, polyacrylic acids, polyvinylpyrrolidone or polyethylenimine can also be used in place of or in addition to the high molecular weight PVOH, in the same relative proportions.

EXAMPLE 1

Control: Eighty parts of 98% hydrolyzed polyvinyl alcohol (Aldrich Catalog No. 34,840-6, average Mw=13,000~23,000 dalton/mol) were mixed with twenty parts of 99.6% pure glycerol (Fisher Scientific). The resulting mixture was ground for ten minutes in a mortar. About 20 grams of the mixture was placed between two stainless steel plates with a stainless steel spacer with a thickness of 1 mm. Temperature and pressure were gradually applied. The final pressure was about 40,000 psi and the final temperature was about 200° C., and were applied for about one minute. The temperature was rapidly reduced to room temperature by means of a cooling water jacket while pressure was maintained. The resultant polymeric plate (10×10×0.1 cm) exhibited some flexibility but was easily broken when bent beyond 70° angles. DSC measurement using High Resolution DSC 2920 from TA Instruments on this plate shows a glass transition (inflection) of 38° C.

Experiment: Eighty parts of 98% hydrolyzed polyvinyl alcohol (Aldrich Catalog No. 34,840-6, average Mw=13,000~23,000 dalton/mol) were mixed with twenty parts of 3,6,9-oxa-undecanoic diacid (Hoechst Celanese). The same procedure was followed as set forth above for the PVOH/glycerol control mixture. The resultant polymeric plate exhibited more flexibility than the control and did not break until the bending angle exceeded about 140°. The glass transition temperature of this polymeric plate is about 28° C. at the same conditions as the control.

EXAMPLE 2

Control: Eighty parts of 88% hydrolyzed polyvinyl alcohol (Polysciences, Inc., Catalog No. 02975, average molecular weights ~25,000 dalton/mol) were mixed with twenty parts of 99.6% pure glycerol (Fisher Scientific). The hot pressing procedure was the same used for the control of Example 1 above. The resultant polymeric plate (10×10×0.1 cm) exhibited more flexibility than the control of Example 1, but was easily broken when bent at 80° angles.

Experiment: Eighty parts of 88% hydrolyzed polyvinyl alcohol (Polysciences, Inc., Catalog No. 02975, average molecular weights ~25,000 dalton/mol) were mixed with twenty parts of 3,6,9-oxa-undecanoic diacid (Hoechst Celanese). The same procedure was followed as for Example 1. The resultant polymeric plate exhibited more flexibility than the control of this example and did not break until the bending angle exceeded about 85°.

EXAMPLE 3

Experiment: Eighty parts of 98% hydrolyzed polyvinyl alcohol (Aldrich Catalog No. 34,840-6, average Mw=13,000~23,000 dalton/mol) were mixed with twenty parts of polyoxa diacid (n=10~11)(Hoechst Celanese). The same procedure was followed as listed in Example 1. The resultant polymeric plate exhibited more flexibility than the controls and did not break until the bending angle exceeded about 95°.

EXAMPLE 4

Experiment: Eighty parts of 88% hydrolyzed polyvinyl alcohol (Polysciences, Inc., Catalog No. 02975, average molecular weights ~25,000 dalton/mol) were mixed with twenty parts of 3,6,9-oxa-dodecanoic acid (Hoechst Celanese). The same procedure was followed as listed in Example 1 The resultant polymeric plate exhibited more flexibility than the controls and did not break until the bending angle exceeded about 100°.

EXAMPLE 5

Experiment: Eighty parts of 98% hydrolyzed polyvinyl alcohol (Aldrich Catalog No. 34,840-6, average Mw=13,000~23,000 dalton/mol) were mixed with twenty parts of a mixture of oxa acids with a molar ratio of 3,6,9-trioxa-undecanoic acid to polyoxa diacid (n=10~11) equaling 4:1 (Hoechst Celanese). The same procedure was followed as listed in Example 1. The resultant polymeric plate exhibited more flexibility than the controls and did not break until the bending angle exceeded about 95°.

EXAMPLE 6

Experiment: Eighty parts of 88% hydrolyzed polyvinyl alcohol (Polysciences, Inc., Catalog No. 02975, average molecular weights=~25,000 dalton/mol) were mixed with twenty parts of a mixture of oxa acids with a molar ratio of 3,6,9-trioxa-undecanoic acid to polyoxa (n=10~11) diacid equaling 4:1 (Hoechst Celanese). The same procedure was followed as listed in Example 1. The resultant polymeric plate exhibited more flexibility than the control and did not break until the bending angle exceeded about 100°.

These experiments demonstrate the enhanced strength and flexibility provided by the various embodiments of the claimed formulation, in contrast to the control product. This strength and flexibility, shown by progressively greater resistance to breakage when bent, provides a more durable and suitable molded product for a variety of applications, including tampon applicators. The examples also demonstrate that the strength and flexibility of the claimed composition vary somewhat based upon the oxa acid plasticizer and polyvinyl alcohol selected. Namely, most preferred results were achieved by the combination of ~25,000 dalton/mol 88% hydrolyzed polyvinyl alcohol (Polysciences, Inc., Catalog No. 02975) with 3,6,9-oxa-dodecanoic acid and with a mixture of 4:1 3,6,9-trioxa-undecanoic acid to polyoxa (n=10~11) diacid.

The invention having been thus described with particular reference to the preferred forms thereof, it will be obvious that various changes and modifications may be made therein without departing from the spirit and scope of the invention as defined in the appended claims.

What is claimed is:

1. A moldable polymeric compound comprising:
   about 50 to about 99 percent by weight of a polyvinyl alcohol; and
   about 1 to about 50 percent by weight of at least one oxa acid plasticizer.

2. The moldable polymeric compound of claim 1, wherein said polyvinyl alcohol has a degree of polymerization (DP) less than 1200.

3. The moldable polymeric compound of claim 2, said moldable polymeric compound further comprising a second polyvinyl alcohol having a degree of polymerization (DP) of about 1200 or greater.

4. The moldable polymeric compound of claim 1, wherein said plasticizer is selected from the group consisting of oxa monoacids, oxa diacids, diglycolic acids, other linear carboxylic acids with at least one ether group distributed along a linear chain thereof, and a combination thereof.

5. The moldable polymeric compound of claim 4, wherein said diglycolic acid has the following formula:

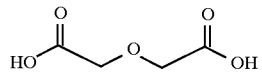

6. The moldable polymeric compound of claim 2, wherein said polyvinyl alcohol has the following formula:

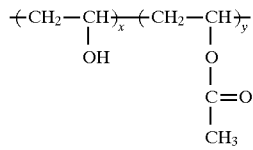

where x=40 to 100 mole percent and y=0 to 60 mole percent.

7. The moldable polymeric compound of claim 1, wherein said moldable polymeric compound is a tampon applicator barrel.

8. The moldable polymeric compound of claim 1, wherein said moldable polymeric compound is a tampon applicator plunger.

9. The moldable polymeric compound of claim 1, further comprising a high molecular weight polymer selected from the group consisting of starch, polyacrylic acids, polyvinylpyrrolidone, polyethylenimine, and a combination thereof.

10. The moldable polymeric compound of claim 1, wherein said oxa acid plasticizer has the following formula:

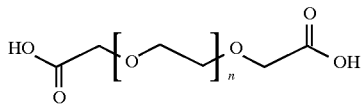

where n=0~1000.

11. The moldable polymeric compound of claim 10, wherein said oxa acid plasticizer is selected from the group consisting of 3,6,9-oxa-undecanoic diacid, 3,6,9-oxa-dodecanoic acid, 3,6,9-trioxa-undecanoic acid, polyoxa diacid (n=10~11), and combinations thereof.

12. A tampon applicator comprising:
    about 50 to about 99 percent by weight of a polyvinyl alcohol; and
    about 1 to about 50 percent by weight of at least one oxa acid plasticizer.

13. The tampon applicator of claim 12, wherein said polyvinyl alcohol has a degree of polymerization (DP) less than 1200.

14. The tampon applicator of claim 13, further comprising a second polyvinyl alcohol having a degree of polymerization (DP) of about 1200 or greater.

15. The tampon applicator of claim 12, wherein said plasticizer is selected from the group consisting of oxa monoacids, oxa diacids, diglycolic acids, other linear carboxylic acids with at least one ether group distributed along a linear chain thereof, and a combination thereof.

16. The tampon applicator of claim 15, wherein said diglycolic acid has the following formula:

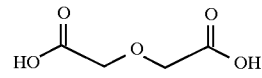

17. The tampon applicator of claim 13, wherein said polyvinyl alcohol has the following formula:

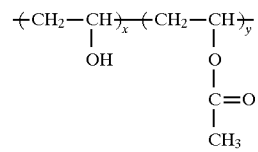

where x=40 to 100 mole percent and y=0 to 60 mole percent.

18. The tampon applicator of claim 12, further comprising a high molecular weight polymer selected from the group consisting of starch, polyacrylic acids, polyvinylpyrrolidone, polyethylenimine, and a combination thereof.

19. The tampon applicator of claim 12, wherein said oxa acid plasticizer has the following formula:

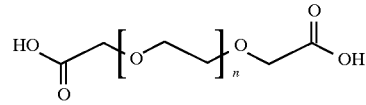

where n=0~1000.

20. The tampon applicator of claim 19, wherein said oxa acid plasticizer is selected from the group consisting of 3,6,9-oxa-undecanoic diacid, 3,6,9-oxa-dodecanoic acid, 3,6,9-trioxa-undecanoic acid, polyoxa diacid (n=10~11), and combinations thereof.

21. A method for manufacturing biodegradable polymeric articles comprising:
    mixing about 50 to about 99 percent by weight of a polyvinyl alcohol and about 1 to about 50 percent by weight of at least one oxa acid plasticizer to form a mixed composition, and
    molding said articles from said mixed composition.

22. The moldable polymeric compound of claim 3, wherein said second polyvinyl alcohol is present at about 1 to about 40 percent by weight.

23. The moldable polymeric compound of claim 3, wherein said second polyvinyl alcohol has a degree of polymerization (DP) from about 1200 to about 2400.

24. The moldable polymeric compound of claim 9, wherein said high molecular weight polymer is present at about 1 to about 40 percent by weight.

25. The tampon applicator of claim 14, wherein said second polyvinyl alcohol is present at about 1 to about 40 percent by weight.

26. The tampon applicator of claim 14, wherein said second polyvinyl alcohol has a degree of polymerization (DP) from about 1200 to about 2400.

27. The tampon applicator of claim 18, wherein said high molecular weight polymer is present at about 1 to 40 percent by weight.

28. The method of claim 21, further comprising simultaneously mixing up to about 40 percent by weight of a second polyvinyl alcohol with the about 50 to about 99 percent by weight of said polyvinyl alcohol and the about 1 to about 50 percent by weight of said at least one oxa acid plasticizer to form the mixed composition.

29. The method of claim 21, further comprising simultaneously mixing up to 40 percent by weight of a high molecular weight polymer with the about 50 to about 99 percent by weight of said polyvinyl alcohol and the about 1 to about 50 percent by weight of said at least one oxa acid plasticizer to form the mixed composition.

30. The moldable polymeric compound of claim 23, wherein said second polyvinyl alcohol is present at about 1 to about 40 percent by weight.

31. The tampon applicator of claim 26, wherein said second polyvinyl alcohol is present at about 1 to about 40 percent by weight.

* * * * *